United States Patent [19]
McIntyre et al.

[11] Patent Number: 6,048,091
[45] Date of Patent: Apr. 11, 2000

[54] ATMOMETER

[75] Inventors: Graeme N. McIntyre; Herbert Bruce Penfold, both of New Lambton; Gary Douglas Worth, Salt Ash; Franz Holawe, Amstetten, all of Australia

[73] Assignee: The University of Newcastle Research Associates Limited, Newcastle, Australia

[21] Appl. No.: 08/875,020

[22] PCT Filed: Dec. 22, 1995

[86] PCT No.: PCT/AU95/00878

§ 371 Date: Sep. 22, 1997

§ 102(e) Date: Sep. 22, 1997

[87] PCT Pub. No.: WO96/20397

PCT Pub. Date: Jul. 4, 1996

[30] Foreign Application Priority Data

Dec. 23, 1994 [AU] Australia ........................................ 0275
Sep. 18, 1995 [AU] Australia ........................................ 5485

[51] Int. Cl.[7] ........................... G01N 25/56; G01N 33/18; G01N 19/10

[52] U.S. Cl. ........................... 374/54; 73/61.77; 261/104
[58] Field of Search ........................... 73/61.77, 198, 73/223, 224; 137/391–396; 261/104; 374/54

[56] References Cited

U.S. PATENT DOCUMENTS

| 4,324,132 | 4/1982 | Williams . |
| 4,709,585 | 12/1987 | Altenhofen . |
| 5,311,769 | 5/1994 | Hetzel . |
| 5,389,311 | 2/1995 | Hetzel . |
| 5,423,206 | 6/1995 | Hetzel ........................................ 73/61.77 |

*Primary Examiner*—Vit Miska
*Attorney, Agent, or Firm*—Holland & Hart LLP

[57] ABSTRACT

An atmometer includes a chamber having arranged in an interior region thereof a medium in fluid communication with a liquid source and adapted for releasably retaining liquid. The chamber also has at another region an opening to the surrounds over which a gas permeable medium is arranged. In one mode of use, the atmometer is positionable such that ambient air moving over the gas permeable medium causes at least a portion of any evaporated liquid in the chamber to diffuse through the gas permeable medium.

22 Claims, 2 Drawing Sheets

ATMOMETER

FIELD OF THE INVENTION

The present invention relates to an atmometer, and in particular to a gas exchange atmometer for determining water loss to the atmosphere through transpiration in plants, crops, soil etc in the agricultural environment, and in other environments where transpiration evaporation and humidity levels need to be determined (e.g. a baby's humidicrib). The invention will be described in the agricultural context, but it should be appreciated that the invention is not limited to such applications.

BACKGROUND ART

An atmometer is an instrument used or measuring evaporation. Atmometers have been known for some time, and can either be of a design whereby measurement of the rate of evaporation of water from a wet surface is determined or measurement of the rate of evaporation of water through a porous surface is determined. In the past, problems have been experienced in obtaining accurate and reproducible readings from atmometers, and it has been proposed in the scientific literature that existing atmometers are susceptible to windy conditions, causing inaccuracies in readings.

It has become increasingly important to simulate and estimate vapour loss through transpiration in plants, particularly plants subjected to, or growing in, dry environments. Transpiration from a plant leaf is a two-stage process. Moisture first evaporates from a wet surface of parenchyma cells within the leaf, which cells are surrounded by air spaces necessary for exchange of gasses during photosynthesis. Typically water evaporated into the small amounts of air in these spaces is at saturation vapour pressure for the temperature of the leaf. In the second stage of this process, the saturated air diffuses from within the leaf through the stomatal openings in the leaf surface and mixes with ambient air to be removed by wind action.

It would be advantageous if an instrument could be provided that at least partially simulates this process to provide some indication of the evaporation of water in agricultural environments.

SUMMARY OF INVENTION

The present invention provides an atmometer including a chamber having arranged in an interior region a medium in fluid communication with a liquid source and adapted for releasably retaining liquid, the chamber also having at another region an opening to the surrounds over which a gas permeable medium is arranged, in one mode of use the atmometer being positionable such that ambient air moving over the gas permeable medium causes at least a portion of any evaporated liquid in the chamber to diffuse through the gas permeable medium.

When the term "gas permeable medium" is used throughout the present specification, it includes a medium that is permeable to both gas and vapour.

By employing such a chamber in said one mode of use, the effects of wind may be at least partially ameliorated.

It is preferred that the medium is a pad arranged at a first side wall of the chamber adjacent to and covering a chamber inlet for the liquid source. In this regard, the pad can be configured so that the liquid source supplies sufficient liquid thereto and such that, in use, gas within the chamber is saturated with the vapour from the liquid, for a given ambient temperature and pressure. With an atmometer so configured, the conditions occurring in the two-stage transpiration process in a leaf can be closely simulated.

It is preferred that the gas permeable medium is arranged to cover an opening in a side wall of the chamber opposing the first side wall. By arranging the gas permeable medium in this way, a humidified environment (preferably approaching 100% relative humidity) can be achieved in the chamber.

Preferably one or more electrodes are applied to or are incorporated within the pad and are adapted for providing in use an electrical signal that is indicative of pad liquid content and/or variations thereof through the pad.

In this regard a fluid control circuit can be connected to the chamber inlet and can be adapted for responding to the electrical signal so as to feed liquid to the pad to maintain a predetermined liquid content therein.

In this way the atmometer can be supplied as a robust, fully integrated unit for use in electronic control procedures used in agriculture, horticulture, etc. The atmometer can be used to determine evaporation continuously, and, for example, may be operated remotely, or as cart of an overall agricultural control procedure.

Alternatively, the chamber inlet for the liquid source can be connected to a feed tube for holding the liquid source, with a wick extending from the pad, through the chamber inlet, the feed tube and into the liquid source. By employing a wick with a feed tube, wicking effects can be induced in the atmometer to continuously supply the membrane pad with liquid.

Preferably the liquid is water and the gas within the chamber is air. The medium and the wick can he formed from towelling-type material and the gas permeable medium can be formed from a woven material (eg. polymeric woven material) or cloth.

BRIEF DESCRIPTION OF DRAWINGS

Notwithstanding any other forms which may fall within the scope of the present invention, preferred forms of the invention will now be described, by way of example only, with reference to the accompanying drawings and non-limiting examples in which.

MODES FOR CARRYING OUT THE INVENTION

A preferred form of the invention will be described with reference to an atmometer used for simulating transpiration rates from leaves. However, preferred atmometers according to the invention can be used in the study of soil and atmospheric moisture in and around vegetation, and especially in agricultural crops. Indeed atmometers according to the invention can be used wherever evaporation, transpiration or humidity levels need to be monitored (e.g. as part of an alarm circuit in a hospital humidicrib for babies etc.) The electronic versions of the atmometer find particularly wide application. The small size, low cost and ease of manufacture of the preferred atmometers according to the invention can enable it to be used in the evaluation of two and/or three dimensional distribution of moisture fluxes within vegetation canopies and around individual plants. This evaluation can also extend to the monitoring of irrigation, the salination of soils, the estimation of bushfire risks and the monitoring of the performance of indoor ornamental plants etc. Thus, the preferred atmometers have a wide variety of applications.

Major environmental factors controlling transpiration rates from leaves are sensible heat flow, solar radiation and wind turbulence. Thermal energy input promotes transpiration losses by increasing the saturation vapour pressure within a leaf and thus increases the vapour pressure gradient so that the rate of diffusion through the leaf stomates is correspondingly increased. Light energy input has a similar effect and also promotes photosynthesis, which in turn influences the degree of stomatal opening. Wind turbulence removes saturated air from the surface of leaves thus maintaining the vapour pressure gradient. Thus, an atmometer should simulate these effects to provide an accurate indication of transpiration rates. At the same time, the over-reaction to wind flow and atmometer variability needs to be addressed if the atmometer is to provide accurate readings.

Figure 1:
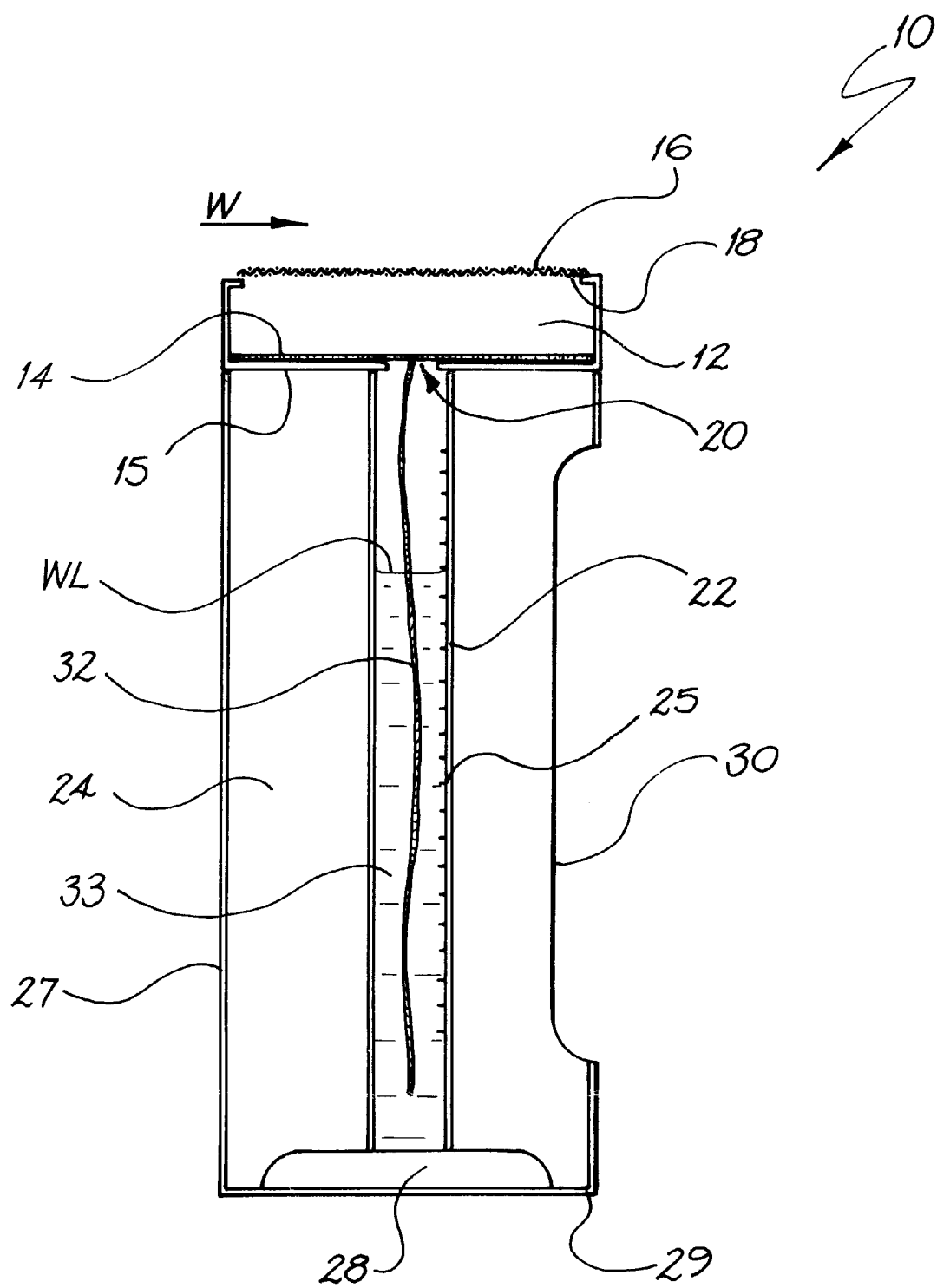
FIG. 1 shows a side sectional view of one type of atmometer according to the invention.

Referring to FIG. 1 of the drawings, an atmometer 10 includes a humidified chamber 12, which has a pad 14 arranged at a base 15 thereof, and a gas permeable cloth cover 16 arranged over an opening 18 in the upper part of the chamber 12.

Base 15 has a hole 20 formed therethrough, and a feed tube 22 registers with this hole and extends downwardly from the underside of base 15 and within a second chamber 24. The feed tube has a plurality of gradations 25 formed on one side thereof for ease of reading liquid level in the tube by a user of the device. The feed tube can simply be aligned to stand under the hole 20 or can additionally be fastened to the underside of base 15 through any appropriate fixing system (eg. glue, plastic welding, clamping, stapling, snap or screw hastening, etc).

The chamber 12 can be attached to a container 27 (eg. formed from a plastics (eg. PVC) material), once again using a fixing system as defined above. The container is preferably sized such that the feed tube fits wholly therewithin (as so that a base stand 28 of the feed tube sits at the base 29 of the container. Thus, as another alternative the base stand 28 can be fastened to the base 29 so that the feed tube opening is brought into alignment with the hole 20 when the chamber 12 is fitted to the container 27. A cut-out portion 30 can be formed in the container 27 to facilitate and enable easy viewing of the gradations 25 on the feed tube.

A wick 32 is attached to and extends downwardly from pad 14, through hole 20, tube 22 and into liquid 33 held in the feed tube; (in most cases the liquid is water or a water-based solution, but in some special applications may be an organic solvent). The wick length is selected such that in use, a portion of the wick is always submerged below the water level WL.

Thus the pad is kept moist with fluid by virtue of the wicking action of fluid from the tube liquid up the wick and to the pad. In this regard, it is preferred that the wick and pad are formed of the same material, preferably a material with good wicking properties such as towelling (eg. cotton towelling).

In use the atmometer can be "primed" by applying a small amount of water to the pad 14 to "wet up" the pad. The wick then maintains the pad moist during use.

Typically, the rate and amount of evaporation occurring can be determined in pre-determined interval(s) by reading the level WL against a gradation 25 and comparing this against previous level(s). Loss of liquid from the feed tube can thus be read directly and accordingly can be converted (correlated) to evaporation loss as depth (mm). As a backup or as an alternative, the atmometer can also be weighed initially, and weighed again at the predetermined interval(s) to calculate weight (and thus amount) of liquid loss.

The atmometer of initial and known liquid level (and optionally, known weight) is placed in situ (eg. adjacent a plant, in a field testing situation etc). A portion of the water in the pad 14 then tends to evaporate and eventually brings the humidified chamber 12 to saturation for the given ambient temperature and pressure. Any wind present will tend to move across the atmometer generally in the direction as indicated by arrow W, and the water vapour will tend to diffuse from the atmometer by exiting the humidified chamber 12 via gas permeable cloth cover 16. This exiting water vapour will be replaced by evaporation from the pad, and in turn the water loss from the pad will be replaced by water from the feed tube (ie. moving up wick 32 to the pad via a wicking action). As the water level drops in the feed tube its level can be periodically read, and evaporation loss can be calculated.

The periods of time for reading are determined by the nature of the particular field trial study, testing experiment etc. At each period the atmometer can also be re-weighed, with the weight difference also providing an indication of the amount of water that has been transpired by adjacent plants, soil etc in that environment.

Figure 2:
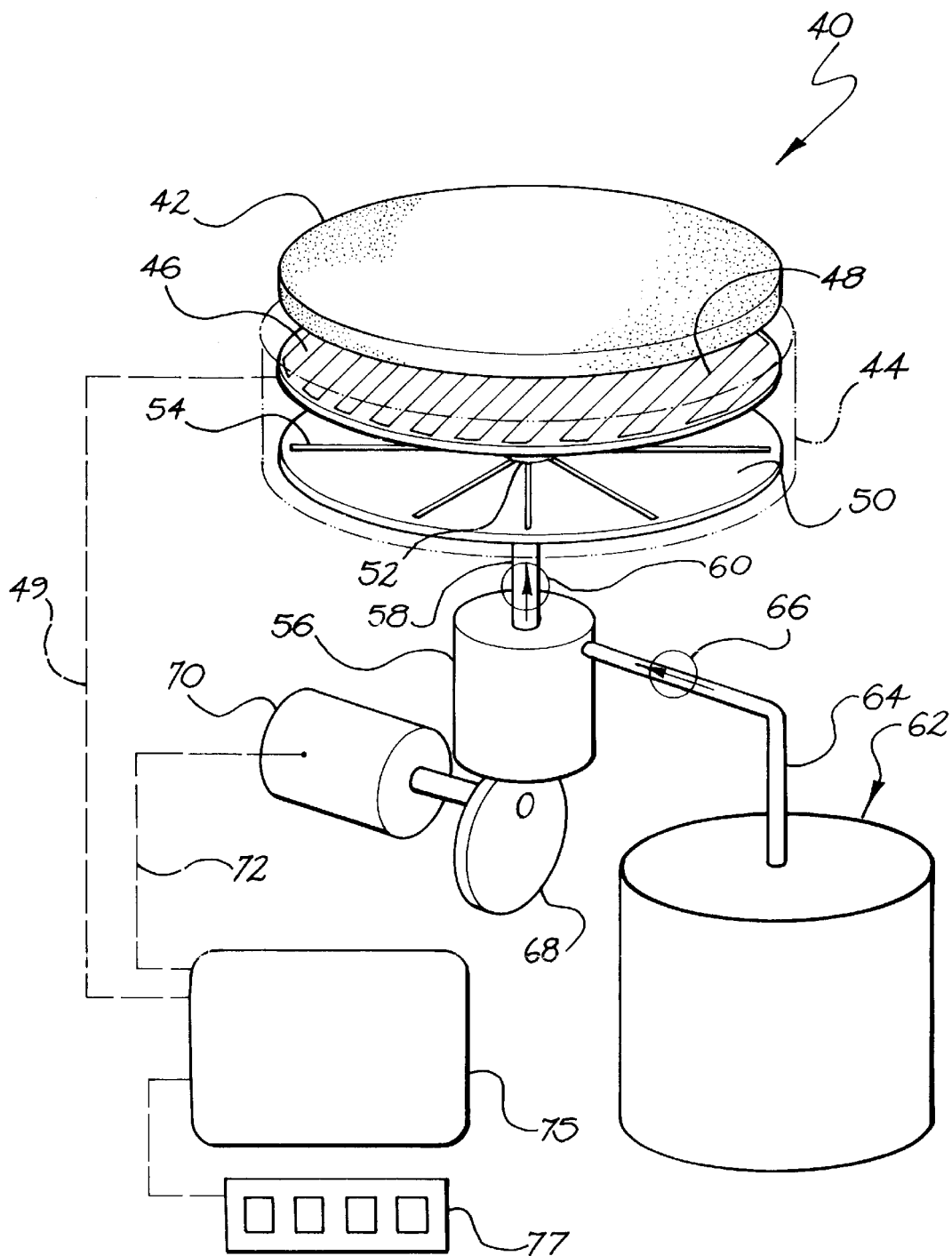
FIG. 2 shows a schematic perspective view of another preferred type of atmometer according to the invention.

Referring to FIG. 2, a schematic perspective view of an alternative and more preferred atmometer 40 is shown. The atmometer 40 employs a membrane in the form of relatively thicker pad 42. The components of chamber 44 are shown in an exploded manner for the sake of clarity.

Underlying pad 42 is a sensor plate 46. The sensor plate includes a base formed from an insulating material, and has a plurality of conducting tracks 48 printed on an upper surface of the base, most preferably in an electrical resistance grid formation. In addition, it is most preferable that the sensor plate be adapted to allow liquid to permeate therethrough, and this can be achieved most favourably by forming a plurality of perforations through the plate. A suitable material for the sensor plate is Veroboard® substrate (Registered Trade Mark of BLCC-Vero Electronics Limited). The sensor plate is coupled to an electronic circuit via electrical signal wiring 49 (as described below).

The base 50 of the chamber 44 can incorporate one or more holes 52 therein for the through flow of liquid from a liquid source (described below). Extending from the or each hole are a plurality of channels 54 which distribute liquid fed to the chamber generally evenly on the underside of sensor plate 46 and thus evenly to the pad 42.

Fluid is pumped into the chamber from pump 56 via conduit 58. To prevent fluid back flow to the pump, a non-return valve 60 is arranged in the conduit 58 and allows fluid flow only in the direction as indicated by the arrow.

The pump receives liquid from a liquid reservoir 62 which is connected thereto via supply conduit 64. The supply conduit also includes a non-return valve 66, once again which only allows fluid flow in the direction as indicated by the arrow.

The pump is driven by an eccentric cam 68 which in turn is coupled to a motor 70 as shown. The cam acts on the pump using a conventional drive mechanism. In this regard, the pump can be any one of a piston, diaphragm or rotary type puma. Electrical power supply 72 to the motor 70 is regulated by an electronic control circuit 75. The control circuit is also electrically coupled to the sensor plate via wiring 49 to receive electrical impulses therefrom, (being the return signal of an is outgoing current signal sent from the control circuit to the sensor plate). The control circuit is set up to sense (or detect) the resistance variation between conducting tracks (which are alternately electrically connected) thereby providing an indication of resistance variation across the pad (i.e. due to liquid variation throughout the pad). When the pad is used with water or an aqueous base solution, (e.g. a salt solution) this signal can provide an indication of moisture variation throughout (or liquid content in) the pad. The control circuit can also be programmed (e.g. through any conventional electronic memory) to ensure that a certain moisture or liquid level is maintained in the pad. For example, when a lower liquid content level is detected, (i.e. that is lower than some predetermined level necessary to simulate evaporation) the control circuit activates the pump via electrical power supply 72 so that liquid is fed into the chamber via base 50 and channels 54, through the sensor plate and to the pad. When the control circuit measures that the pad resistance has reached its previously predetermined range, the electrical power supply to the motor is shut off.

The number of times the pump is activated can be monitored by a counting device 77. This count can be interpreted either visually by an operator or by a microprocessor controller as a measure of liquid evaporated from the chamber over a period of time. Alternatively, the count can be read directly from a switch on the cam or associated therewith that monitors motor and cam rotation.

Rather than employing a sensor plate, a plurality of electrodes (e.g. carbon electrodes) arranged under the pad and directly in contact therewith car be provided and electrical resistance between any predetermined pair of electrodes can be used to monitor liquid content in the pad.

Furthermore, resistance detection contacts in addition to or separately of such electrodes can be is employed. These contacts can be arranged on the side of the chamber 12 or on top of or within the pad itself. Once again, these resistance detection contacts can be used to measure the resistance through the pad.

Where the pad is a relatively thicker pad (e.g. up to 1 cm thick) the moisture or liquid content variation at the top and bottom of the mad can be measured to provide a differential, and this can set up a control response in the electronic control circuit where the differential is not within predetermined range(s).

The pad of FIG. 2 can be formed from any suitable absorbent material, including filter-type paper materials, absorbent fibrous materials including natural fibres, polymeric fibres, etc. More suitable materials are likely to include natural fibres as these are more likely to simulate the conditions in a plant-leaf.

The atmometers described above can be operated or incorporated in an overall agricultural control procedure. For example, the atmometer may be part of a feedback control system, so that when evaporation exceeds a certain level, a crop irrigation sprinkler system is activated. In this regard, liquid level readers or electronic atmometer weighing apparatus may also be employed as part of the control circuit.

The atmometer is typically incorporated in a robust, self-contained unit, wherein transpiration is determined or calculated and visually displayed automatically in the unit (eg. through appropriate electronic or microprocessor-type circuitry). The atmometer can also be operated and activated remotely which can be especially advantageous in large-scale agricultural applications.

EXAMPLES characteristics of the instruments of FIGS. 1 and 2 were investigated by comparing their evaporative response under varying environmental conditions with those of several different species of plants, namely purple top (*Verbena bonariensis*), taro (*Colocasia esculenta*), dandelion (*Taraxacum officinale*) and black nightshade (ie. *Solanum nigricum*); (see Table 1 below).

The performance of the atmometers (designated in Table 1 as GE—ie. for gas exchange) is shown in Table 1 using correlation coefficients, being the degree of correlation between the atmometer and the actual transpiration for the given plant. These coefficients indicate that a high degree of correlation can be achieved, and further indicate that the instruments are highly accurate over a wide variety of atmospheric conditions.

TABLE 1

CORRELATION COEFFICIENTS (r) FOR GE ATMOMETER-PLANT COMPARISONS

|  | r | degrees of freedom |
| --- | --- | --- |
| GE & Purple Top | r = 0.9689 | 6 |
| GE & Taro | r = 0.9865 | 6 |
| GE & Dandelion | r = 0.9866 | 6 |
| GE & Black Nightshade | r = 0.8949 | 6 |

In the experiments, established specimens of the four garden plants were set up as micro-lysimiters in small (50 mm diameter) pots and the surrounding soil was covered with plastic film to eliminate surface evaporation. These pots were then placed beside the atmometers, 75 cm above a mown grass surface at a site where boundary layer turbulence was minimal.

Transpiration was determined by visual and weight loss techniques, measured hourly (to an accuracy of 0.01 gms on an electronic balance). Relative humidity and wind velocity were also measured hourly.

During the test both the plants and atmometers responded to naturally varying levels of direct and indirect solar radiation and were presumed to be actively photosynthesising whenever there was sufficient light. Wind velocities also varied up to 10 m/second.

Referring to Table 1, the lower correlation observed between the atmometer and the plant solanum were surmised to be due to an adverse reaction of the plant to the experimental procedures, possibly due to elevated root temperature.

Whilst the invention has been described with reference to a number of preferred embodiments, it should be appreciated that the invention can be embodied in many other forms.

We claim:

1. An atmometer including a chamber having arranged in an interior region a medium in fluid communication with a liquid source and adapted for releasably retaining liquid, the chamber also having at another region an opening to the surrounds over which a gas permeable medium is arranged, in one mode of use the atmometer being positionable such that ambient air moving over the gas permeable medium causes at least a portion of any evaporated liquid in the chamber to diffuse through the gas permeable medium.

2. An atmometer as claimed in claim 1, wherein the medium is a pad arranged at a first side wall of the chamber adjacent to and covering a chamber inlet for the liquid source.

3. An atmometer as claimed in claim 2, wherein the pad is configured so that the liquid source supplies sufficient liquid thereto and such that, in use, gas within the chamber is saturated with the vapour from the liquid, for a given ambient temperature and pressure.

4. An atmometer as claimed in claim 2, wherein the gas permeable medium is arranged to cover an opening in a side wall of the chamber opposing the first side wall.

5. An atmometer as claimed in claim 2 wherein one or more electrodes are applied to or are incorporated within the pad and are adapted for providing in use an electrical signal that is indicative of pad liquid content and/or variations thereof through the pad.

6. An atmometer as claimed in claim 5 wherein a fluid control circuit is connected to the chamber inlet and is adapted for responding to the electrical signal so as to feed liquid to the pad to maintain a predetermined liquid content therein.

7. An atmometer as claimed in claim 6 wherein the fluid control circuit includes a liquid reservoir, a pump operable between the chamber inlet and the liquid reservoir and arranged such that activation of the pump causes liquid to be pumped from the reservoir to the pad via the chamber inlet, and a pump motor control unit which is adapted for receiving electrical signal and activating and driving the pump in a manner that maintains the predetermined liquid content in the pad.

8. An atmometer as claimed in claim 7 wherein the pump motor control unit includes a separate motor arranged for driving the pump and a programmable control circuit that is responsive to the electrical signal to activate the motor, which in turn activates the pump.

9. An atmometer as claimed in claim 7 wherein the pump is a piston, diaphragm or rotary-type pump.

10. An atmometer as claimed in claim 6 wherein the one or more electrodes are in the form of:

(a) a sensor plate including an insulating material base, and a plurality of conductive tracks formed on one side of the base to define a resistance grid, the tracks being alternately electrically connected such that with a supply of electrical current therethrough, an electrical signal that is indicative of variation of pad liquid content can be produced, the plate being positionable under the pad in use with the tracks facing the pad underside;

(b) one or more resistance detection contact pairs, the or each pair being opposed across the pad and adapted in use to measure resistance through the pad to provide said electrical signal; and/or (c) electrodes directly applied to the pad that directly measure electrical resistance between selected electrode pairs to provide said electrical signal.

11. An atmometer as claimed in claim 10 wherein in (b) the one or more resistance detection contact pairs are:

(i) mounted at the side of the chamber, (ii) arranged on top of the pad; and/or (iii) when the pad is sufficiently thick, mounted on sides of the pad.

12. An atmometer as claimed in claim 6 wherein the one or more electrodes are adapted in use for measuring liquid content on the top and bottom of the pad such that any difference in pad liquid content between the top and bottom generates a signal that causes the fluid control circuit to supply further liquid to the pad via the chamber inlet.

13. An atmometer as claimed in claim 4, wherein the chamber inlet for the liquid source is connected to a feed tube for holding the liquid source, with a wick extending from the pad, through the chamber inlet, the feed tube and into the liquid source.

14. An atmometer as claimed in claim 13 wherein the feed tube is graduated such that the volume of liquid wicked from the liquid source to the pad by the wick can be directly ascertained.

15. An atmometer as claimed in claim 13, wherein the chamber in use is arranged on top of an upper end of an elongate container with the opening being positioned in the in-use upper end of the chamber and the inlet positioned in the in-use lower end of the chamber, with the feed tube extending vertically downwards from the inlet and within the elongate container.

16. An atmometer as claimed in claim 15, wherein a portion of the elongate container side wall is removed to enable viewing of liquid level within the feed tube.

17. An atmometer as claimed in claim 1, wherein the medium is formed from a towelling-type material.

18. An atmometer as claimed in claim 13, wherein the wick is formed from a towelling-type material.

19. An atmometer as claimed in claim 1, wherein the liquid is water and gas within the chamber is air.

20. An atmometer as claimed in claim 1, wherein the gas permeable medium is a woven material.

21. An atmometer as claimed in claim 20, wherein the woven material is a polymeric cloth material.

22. A chamber for use in an atmometer, the configuration of the chamber being as defined in claim 1.

* * * * *